(12) United States Patent
Chiribiri

(10) Patent No.: US 11,361,430 B2
(45) Date of Patent: Jun. 14, 2022

(54) SYSTEM AND METHOD FOR MEDICAL IMAGING

(71) Applicant: KING'S COLLEGE LONDON, London (GB)

(72) Inventor: Amedeo Chiribiri, London (GB)

(73) Assignee: KING'S COLLEGE LONDON, London (GB)

(*) Notice: Subject to any disclaimer, the term of this patent is extended or adjusted under 35 U.S.C. 154(b) by 111 days.

(21) Appl. No.: 16/606,160

(22) PCT Filed: Apr. 18, 2018

(86) PCT No.: PCT/GB2018/051014
§ 371 (c)(1),
(2) Date: Oct. 17, 2019

(87) PCT Pub. No.: WO2018/193245
PCT Pub. Date: Oct. 25, 2018

(65) Prior Publication Data
US 2020/0372634 A1    Nov. 26, 2020

(30) Foreign Application Priority Data
Apr. 18, 2017    (GB) .................................... 1706149

(51) Int. Cl.
*G06T 7/00*    (2017.01)
*G06T 7/11*    (2017.01)
(Continued)

(52) U.S. Cl.
CPC .............. *G06T 7/0012* (2013.01); *G06T 7/11* (2017.01); *G16H 50/20* (2018.01); *G16H 50/30* (2018.01);
(Continued)

(58) Field of Classification Search
CPC ..................... G06T 7/0012; G06T 7/11; G06T 2207/10081; G06T 2207/10088;
(Continued)

(56) References Cited

U.S. PATENT DOCUMENTS 9,179,881 B2    11/2015    Menon Gopalakrishna et al.
2007/0014452 A1*    1/2007    Suresh .................... G06T 7/246
382/128

(Continued)

FOREIGN PATENT DOCUMENTS

| WO | 2005/004066 A1 | 1/2005 |
| WO | 2015/049324 A1 | 4/2015 |
| WO | 2018/193245 A1 | 10/2018 |

OTHER PUBLICATIONS

Chiribiri et al., "Perfusion dyssynchrony analysis," European Heart Journal—Cardiovascular Imaging, 2016, pp. 1414-1423, vol. 17.
(Continued)

*Primary Examiner* — Emily C Terrell
*Assistant Examiner* — Molly Delaney
(74) *Attorney, Agent, or Firm* — Polsinelli PC

(57) ABSTRACT

A system and for determining the presence or absence of myocardial ischemia in a subject, based upon analysis of medical images of at least one region of the heart of a subject of interest, the plurality of medical images being acquired in a consecutive manner by a medical imaging modality and being a plurality of myocardial layers in a direction which is generally perpendicular to the wall of the left ventricular myocardium.

15 Claims, 2 Drawing Sheets

(51) Int. Cl.
*G16H 50/30* (2018.01)
*G16H 50/20* (2018.01)
(52) U.S. Cl.
CPC .............. *G06T 2207/10081* (2013.01); *G06T 2207/10088* (2013.01); *G06T 2207/10108* (2013.01); *G06T 2207/20021* (2013.01); *G06T 2207/30048* (2013.01); *G06T 2207/30104* (2013.01)
(58) Field of Classification Search
CPC . G06T 2207/10108; G06T 2207/20021; G06T 2207/30048; G06T 2207/30104; G06T 2207/10072; G06T 2207/30101; G06T 7/0016; G16H 50/30; G16H 50/20
See application file for complete search history.

(56) References Cited

U.S. PATENT DOCUMENTS

| | | | | |
|---|---|---|---|---|
| 2016/0235330 | A1* | 8/2016 | Breeuwer | A61B 8/06 |
| 2018/0218497 | A1* | 8/2018 | Golden | G06T 7/11 |
| 2020/0193603 | A1* | 6/2020 | Golden | G06T 7/149 |

OTHER PUBLICATIONS

International Search Report and Written Opinion relating to International Application No. PCT/GB2018/051014, dated Jul. 6, 2018; 13 pgs.
Search Report relating to GB Application No. 1706149.0, dated Sep. 29, 2017; 3 pgs.

* cited by examiner

SYSTEM AND METHOD FOR MEDICAL IMAGING

CROSS-REFERENCE TO RELATED APPLICATIONS

This application is a U.S. National Stage Application of International Application No. PCT/GB2018/051014, filed Apr. 18, 2018, which claims priority from GB Patent Application No. 1706149, filed Apr. 18, 2017, the entire contents of which are hereby incorporated by reference in their entirety.

FIELD OF THE INVENTION

The invention relates to the field of medical imaging of the heart, and in particular to the field of analyzing medical images of the heart, to systems, methods and elements used in this field.

BACKGROUND OF THE INVENTION

First-pass enhancement imaging of the heart by cardiac magnetic resonance (CMR) imaging, and more recently also cardiac computed tomography (CCT) imaging or single photon emission computed tomography (SPECT), allows for the visualization and quantification of myocardial perfusion. The identification of areas of tissue with impaired perfusion is based either on image interpretation performed by expert readers or on the quantification of areas of ischemia. This quantification includes semi-quantitative or true quantitative analysis of time-intensity curves. Semi-quantitative analysis comprises quantification of several characteristic features of time-intensity curves, for instance peak intensity, maximum upslope, mean transit time, and others. In true quantitative analysis, the actual myocardial blood flow is calculated from a mathematical analysis of the arterial input function (AIF) and the time-intensity curves obtained in the myocardium. An extensive review of both semi-quantitative and true quantitative approaches is given in Jerosch-Herold: Quantification of myocardial perfusion by cardiovascular magnetic resonance, Journal of Cardiovascular Magnetic Resonance 2010, 12:57.

Visual assessment of perfusion images requires the interpretation of expert operators, trained over several years of experience. The availability of such expert readers is roadblocking to a widespread use of CMR and CCT perfusion techniques. Semi-quantitative and quantitative analysis methods are difficult to use and rely on physical, physiological and mathematical assumptions to provide correct measurements of myocardial blood flow. These assumptions might not always hold true and the results of these analyses do not necessarily yield true quantitative measurements of myocardial perfusion. There is a need for robust methods to identify abnormal myocardial perfusion that are both robust in their modelling assumptions and suitable for automatization. In general, myocardial ischemia is identified as an absolute reduction of myocardial perfusion or as a reduction relative to a normal area of reference.

Previously, invasive methods for characterization and analysis of myocardial perfusion deficits were often required since non-invasive imaging methods could not reliably differentiate between coronary microvascular dysfunction (MVD) and multi-vessel coronary artery disease (including left main coronary artery disease; CAD). Both these conditions are characterized by diffuse myocardial ischemia, and so previously, distinguishing between these two conditions was carried out by invasive methods. Whilst such methods may be of assistance or necessary in the case of CAD patients, MVD patients were undergoing such procedures unnecessarily, at a significant cost, both in terms of time, money and stress to the patients.

WO2015/049324 describes a method and system for characterizing myocardial perfusion pathology by identifying 'spatio-temporal perfusion inhomogeneity' or 'spatio-temporal dephasing', in order to distinguish between coronary microvascular disease (MVD) and coronary artery disease (CAD).

In 'spatio-temporal perfusion inhomogeneity' or 'spatio-temporal dephasing', which is also known as 'perfusion dyssynchrony' as described in WO2015/049324, medical imaging techniques are used to produce a 'perfusogram' showing the intensity of a signal produced by a contrast agent from a first-pass wave at various positions within different segments of the myocardium over time. These perfusograms are then used to create a series of intensity curves, showing the intensity to of the signal over time so that the time it takes the signal to get to a peak intensity (TTPI) in each segment is clear. An index, based upon the amount of difference between the TTPIs in each segment, as compared to that at a reference point, which is usually in the left ventricle, is then calculated. This provides a measure of the temporal dephasing of the perfusion. As would be understood in the art, the term 'segment' used in WO2015/049324 refers to radial segments of the myocardium. Thus a view is taken along the myocardium, which is then divided into radial segments, as illustrated in FIG. 2A hereinafter. Thus, the measurements are taken generally in the direction of blood flow through large epicardial coronary arteries running on the surface of the heart, and perfusion differences amongst such radial segments investigated.

In a normal heart, with normal perfusion, blood flows uniformly through the heart and so the TTPIs from the various radial segments will be similar, and quite close to that at the reference point. As a result, the range of TTPI variance or the TTPI coefficient of variation will be relatively small. However, where blood flow is interrupted or inhibited in a particular area of the heart as a result of CAD, the TTPI will be significantly different in different radial segments of the myocardium, and so the index of TTPI variance (of coefficient of variation) will be larger.

In the individual with CAD, the spatio-temporal distribution of myocardial blood flow in the myocardium is increasingly inhomogeneous. In the individual with MVD instead, the pathologic alteration involves the microscopic circulation and its interaction in systole with myocardial contraction. In this case, perfusion to the epicardial layer is unobstructed and very homogeneous. However, there is a delay in the transmural propagation of the first-pass wave. Similar to CAD, this causes widespread ischemia with delayed intensity rise onset. However, this feature is homogeneous in the temporal domain throughout the myocardium, allowing the non-invasive differentiation between CAD and MVD.

In the case of MVD, the variation in the TTPI may be less diffuse (homogenous perfusion), since the rate of flow through the major vessels of the heart is not significantly affected. Therefore, the variation in the TTPI may be lower, and may be similar to that seen in a normal heart. However, in this case, as the pathologic alteration involves the microscopic circulation and its interaction in systole with myocardial contraction, there may be a delay in the signal, and the signal may not be as strong as in a normal heart due to reduced flow of the first-pass (ischemia).

Therefore, an index based upon the coefficient of variation of the time periods to peak intensity (TTPI) between the reference time and the time until the occurrence of the peak intensity of the intensity curves over time is defined as providing a basis for diagnosis.

The method of WO2015/049324 is empirical in nature in that the index is required to be compared to an index obtained from a 'normal' individual to fully assess the presence of a condition. A 'positive' index, higher than that observed in a normal individual, is indicative of CAD, whilst a 'negative' index, lower than that in a normal individual, is indicative of the presence of MVD.

Furthermore, there is an assumption that the patient is actually suffering from ischemia to start with, as there is no integral means for determining a normal range indicative of the absence of disease. Therefore, the results may still require some expert analysis.

WO2015/049324 suggests also that the myocardial image positions used to calculate the single index could be selected in a direction along the myocardium (i.e. in the direction of blood flow across the large epicardial coronary vessels) and optionally also in a direction across the myocardium.

EP2391986 teaches a system for gradient based image analysis of transmural perfusion in the myocardium may be used for the diagnosis of CAD.

The applicants have appreciated that gathering a specific spatio-temporal perfusion inhomogeneity index information in a different direction through the heart can provide additional diagnostic information, in particular, can be used to differentiate between normally perfused and ischemic hearts and thus diagnose myocardial ischemia itself, as well as assisting in the distinction between CAD and MVD, and in the mapping of scar tissue.

SUMMARY OF THE INVENTION

According to the present invention there is provided a system for determining the presence or absence of myocardial ischemia in a subject, by analyzing medical images of at least one region of the heart of a subject of interest during a first-pass dose of a contrast agent, the plurality of medical images being acquired in a consecutive manner by a medical imaging modality, the system comprising (i) a delineation unit, configured to delineate contours of a selected region of the heart of the subject of interest in the plurality of medical images and to divide the selected region into a plurality of myocardial layers in a direction generally perpendicular to the wall of the left ventricular myocardium; and (ii) an intensity sampler and analyzing unit configured to sample signal intensities of myocardial image positions from the plurality of medical images, and, for each of the myocardial layers, analyse a sampled signal intensity in the selected region over time and compare the results with those obtained at a reference point over time in the left ventricle to determine a first index number indicative of a spatio-temporal perfusion inhomogeneity or perfusion dephasing among at least a subset of the myocardial layers in the said region as compared to a similar index number obtained in a normal heart;

and where said first index number is greater, diagnosing the presence of ischemia.

In particular, the medical imaging modality is selected from a magnetic resonance (MR), computer tomography (CT), positron emission tomography (PET), or single photon emission computed tomography (SPECT) scanner. Such scanners may form part of the system of the invention.

Thus, there is provided a system for determining the presence or absence of myocardial ischemia in a subject, by analyzing medical images of at least one region of the heart of a subject of interest, the plurality of medical images being acquired in a consecutive manner by a medical imaging modality selected from a magnetic resonance (MR), computer tomography (CT), or single photon emission computed tomography (SPECT) scanner, the system comprising (i) a delineation unit, provided for delineating contours of a selected region of the heart of the subject of interest in the plurality of medical images and for dividing the selected region into a plurality of myocardial layers in a direction which perpendicular to the wall of the left ventricular myocardium; and (ii) an intensity sampler and analyzing unit configured for sampling signal intensities of myocardial image positions from the plurality of medical images from a first-pass dose of a contrast agent, and analysing the medical images from the plurality of layers in the selected region over time and comparing the results with those obtained at a reference point in the temporal direction (over time) in the left ventricle to determine a first index number indicative of a spatio-temporal perfusion inhomogeneity or perfusion dephasing among at least a subset of the myocardial layers in the said region as compared to a similar index number obtained in a normal heart; and where said first index number is greater, diagnosing the presence of ischemia.

The system of the invention allows a measurement of perfusion across the myocardium which will be compromised in the case of ischemia generally, irrespective of whether this is due to CAD or MVD. Specifically, inhomogeneity in the perfusion rates in a direction perpendicular to the wall of the left ventricular myocardium will provide an indication that a subject is ischemic. Any inhomogeneities or dyssynchrony in blood flowing transversely across the myocardium will be an indicator that there is hemodynamically relevant coronary disease or microvascular disease resulting in the onset of ischemia in the subject. This is useful to quickly and simply eliminate patients who may have symptoms such as pain which is not a result of heart disease.

Suitably, the first index number is expressed as a coefficient of variation (standard deviation/average) of time periods to peak intensity (TTPI) as described in WO2015/049324 or time to maximum upslope (TTMU) as described in European Heart Journal-Cardiovascular Imaging (2015) doi:10.1093/ehcji/jev326. In another embodiment, the coefficient of variation—defined as the ratio between the standard deviation and the average of the values of TTPI or TTMU in the plurality of positions across the myocardium—can be used instead of the variance as a basis for the index number. These may be compared to similar indices obtained from a normal healthy individual as described in WO2015/049324.

The number of layers analysed using the system of the invention will be 2 or more, for example in excess of 2, such as from 2-50 or 3-50 layers. The greater the number of layers analysed in this way, the clearer any dyssynchrony of perfusion will become.

If required, the system of the invention may be arranged to obtain and analyse images from layers within a plurality of planes in various regions of the heart simultaneously. This will then allow mapping of the heart, and if required, the entire heart in three-dimensions. This process will be particularly useful, in for example, the mapping of areas of scar tissue, as discussed further below.

Where areas of scar tissue are identified, these areas can be eliminated from the calculation of the said first index number.

In a particular embodiment, the system of the invention is arranged to simultaneously acquire a plurality of medical images in a consecutive manner, in a further direction which is generally in the direction of blood flow through large epicardial coronary arteries running on the surface of the heart, wherein the delineation unit is further arranged to provide for segmenting at least a selected part of the heart into a plurality of radial myocardial segments; and the intensity sampler and analyzing unit is further configured to ample and analyse the medical images obtained over time and comparing the results with those obtained at a reference point over time (in the temporal direction) within the left ventricle to determine a second index number indicative of a spatio-temporal perfusion inhomogeneity or perfusion dephasing among at least a subset of radial myocardial segments of the plurality of myocardial segments in the further direction; and thereafter, as compared to a similar index number obtained in a normal or model heart; and where said second index number is greater, recording a positive result.

The second index number can, as described in WO2015/049324, provide a means of non-invasively distinguishing ischemic patients with MVD from those with CAD. Where the second index is positive, indicative of inhomogeneity in the perfusion rates in a direction along the myocardium in the direction of blood flow, a diagnosis that the ischemia is due to CAD is indicated. Where however the second index number is negative, ischemia is likely to be the result of MVD. In this way appropriate treatment of an ischemic patient may be prescribed.

In a particular embodiment, the second index number is compared with a similar index obtained using a 'phantom' or model heart. A particular example of such a phantom is described in WO2014/140547, the content of which is incorporated herein by reference. The indices may be based upon calibration curves prepared for that instrument. As a baseline value, this would be more consistent than values obtained from 'normal' individuals, where some natural variation may be possible.

The applicants have appreciated that a combination of two distinct indices indicative of inhomogeneity, taken in two different directions through the heart, will substantially improve the diagnostic options available. As discussed above, this will enable the diagnosis of ischemia and the differentiation between CAD and MVD to be carried out in a non-invasive single test.

It is preferable to exclude areas of scar tissue from the analysis using the system of the invention. Scar tissue may arise in the myocardium as a result of an earlier injury or trauma such as a myocardial infarction, or it may be present in asymptomatic or mildly; symptomatic hypertrophic cardiomyopathy (HCS) patients. Whilst this may not, in itself, be a cause of CAD, it may restrict blood flow through the vessels of the heart and so show as a positive result for CAD in the test as described in WO2015/049324. Where the existence and location of scar tissue in a patient has already been determined, using conventional methods, the regions containing scar tissue are suitably excluded from the results used to calculate the index numbers using the system of the invention.

However where such areas of scar tissue have not previously been delineated, the system of this embodiment of the invention may be used to provide such identification.

In a particular embodiment, the system is further arranged to correlate the first index number and second index number to provide additional information with regard to the existence of scar tissue.

In particular, where the first index number is negative (in the sense that it is not greater than that obtained in a normal heart) or only slightly positive, but the second index number is positive, this suggests the presence of scar tissue. However, there may be no significant perfusion dyssynchrony in the transverse direction, and so the tissue will may give a negative result for ischemia using the system of the invention. As a result, a correlation of the first and second index numbers can be used to identify scar tissue.

Specifically, where the first index number is negative or only slightly positive, and the second index number is positive, the result is indicative of the presence of scar tissue in the subject in the specific region of the heart where the readings have been taken.

Since the presence of myocardial scar can result in a slight increase of measured dyssynchrony values in both the radial and transmural direction, it may be necessary to do a confirmatory test. This can be done by re-sampling of the data after a period of time, for example, after a period of time from 1 minute to 3 hours, for example after about 5 minutes. This is because the contrast agent such as the gadolinium will be cleared more slowly from scar tissue than healthy tissue, and so it may be expected that there would be a residual signal after time, in any scar tissue. If necessary, during the late resampling, gadolinium (hyper)-enhancement of images may be required in order to detect the residual gadolinium.

Once scar tissue has been detected, additional mapping procedures, including obtaining further examples of first and second index numbers, taking at different positions within the heart. In this way, a map of the heart in three dimensions may be built up.

Alternatively, areas of scar may be analysed or mapped using a different type of imaging modality or type of data acquisition (for example late gadolinium hyperenhancement in MRI). Once identified in this way, it would be possible to exclude the layers and segments affected by the presence of scar tissue from the computation of the first and second index.

Alternatively, scar tissue may be analysed by comparing dyssynchrony data as described above acquired from a heart at rest and compared with that obtained from the same heart under stress, for example as a result of administration of stimulant drugs. The dyssynchrony observed in scar tissue would be expected to be similar in both cases.

In the case where both the first and second index is negative, this would suggest that the heart is normal (no ischemia is occurring), and that any symptoms may be the result of a different condition.

Thus, the results obtainable from the system of this embodiment may be summarized as follows:

|  |  | Transmural Perfusion Dyssynchrony | |
|---|---|---|---|
|  |  | Positive | Negative |
| Radial Perfusion Dyssynchrony (WO2015/049324) | Positive | CAD | No ischemia (Scar) |
|  | Negative | MVD | No ischemia (Normal) |

Thus, the method of the invention provides a particularly effective and useful flexible method, which maximizes the amount of diagnostic information which may be obtained from a non-invasive medical imaging procedure.

Suitably, the MR, CT or SPECT scanner is set to obtain images in the directions used to obtain the first and second indices as described above in a single procedure, although distinct procedures may be carried out if required.

The phrase "spatio-temporal perfusion inhomogeneity" may also be referred to as "spatial-temporal dephasing" or "perfusion dyssynchrony" in this application and shall be understood particularly as the temporal and spatial distribution of inhomogeneous myocardial blood flow in case of a pathologic abnormality.

The step of delineating contours of the selected part of the heart may be carried out manually, semi-automatically or fully automatically. Appropriate segmentation techniques are known in the art and are commercially available.

The subset of myocardial layers of segments may comprise a strict subset of the plurality of myocardial layers or segments like a perfusion territory, or it may comprise the complete myocardium.

Each index number represents an order of acquisition of each one of medical images over time.

Prior to applying the step of delineating contours of the selected part of the heart, the plurality of medical images may have been subjected to an image registration technique to correct for breathing motion of the subject of interest or through-plane motion, as would be understood in the art. Further, the visual intensity readings may be obtained using a suitable filter, as would be understood in the art.

If required, the system may also include means for conducting quantification of myocardial blood flow in each layer or segment of the plurality of layers or segments. The step of conducting true quantification of myocardial blood flow may be carried out according any one of the techniques known in the art. The true quantification of myocardial blood flow in each layer or segment can provide complementary information for characterizing myocardial perfusion pathology. Any scar tissue identified, for example using the system of the invention as described above or using late gadolinium hyperenhancement images, is suitably excluded from the quantification of myocardial blood flow.

The plurality of medical images used in the system of the invention are acquired by first administering a contrast agent or tracer to the subject of interest, and then monitoring the progress of the contrast agent or tracer in its first pass through the heart. Suitable contrast agents or tracers are well known in the art and include any agent that generates a larger signal compared to a baseline when being acquired by either an MR, CT, PET or SPECT scanner, than the tissue of the subject of interest surrounding the agent. Suitable contrast agents may include compounds based upon iodine, lanthanides such as gadolinium, gold, gallium, bismuth, manganese or iron, or positron emitting compounds.

The intensity signals are measured not only in the heart layers or segments, but also in a reference point in the left ventricle of the heart. This because the left ventricle is the location that receives the contrast agent during first-pass and precedes the upslope in the obtained intensity curves for each of the selected myocardial image positions.

As used herein, the term "upslope", refers to the point in time when an intensity of the obtained intensity curves due to the administering of the contrast agent exceeds a predetermined threshold, e.g. of 10%, compared to an intensity without the contrast agent.

In another preferred embodiment, the system further comprises means for automatically determining, for each of the selected myocardial positions, an individual time period relative to a reference time that is determined by the identified reference location until an occurrence of a characteristic feature of the sampled intensity of each of the myocardial image positions. Then, the individual time periods are used in the step of calculating the index number. The characteristic feature may be a point in time of onset of intensity rise, a point in time of peak intensity, or any other characteristic feature that appears suitable to the person skilled in the art. In this way, the index number indicative of the spatio-temporal perfusion inhomogeneity can readily be calculated in an automatic way.

Preferably, the step of calculating the index numbers comprises a calculation of a statistical measure that is indicative of a variation of the time until occurrence of the characteristic feature at each of the individual myocardial positions relative to the time of occurrence of the characteristic feature at the identified reference location. By that, an index number can be provided that describes the spatio-temporal perfusion inhomogeneity among the myocardial layers or segments in a very significant way. The statistical measure may have the form of the variance, customarily used in statistics as a measure of how far a set of numbers spreads out. In this sense, the variance may be the square of the standard deviation of the set of numbers. In general, the statistical measure may have any other form that the person skilled in the art considers suitable for indicating the variation of the time until occurrence of the characteristic feature at each of the individual myocardial positions.

Preferably, the acquiring of the plurality of medical images of at least a portion of the heart of the subject of interest is at least partially synchronized to a cyclic movement of the heart of the subject of interest. For instance, a medical image can be acquired at a fixed amount of time before or after a reference event in the electrocardiogram like the R-peak of the QRS complex. An advantage of this embodiment of the method is that all medical images of the plurality of medical images are taken at a similar status of the heart, so that there is little motion of the myocardial ventricle among the medical images, and the myocardium is rendered relatively stationary.

The system of the invention, may comprise an integral part of a CT or MRI scanner. The magnetic resonance imaging apparatus may advantageously comprise synchronization means for synchronizing an acquiring of medical images to a cyclic movement of the heart of the subject of interest.

Suitably, the system comprises a software module, arranged to carry out the analysis of the images described above. In particular, the steps to be conducted are converted into a program code of the software module, wherein the program code is implementable in a memory unit of a control unit of the medical imaging modality and is executable by a processor unit of the control unit of the medical imaging modality.

The control unit may be the control unit that is customary for controlling functions of the medical imaging modality. The control unit may alternatively be an additional control unit that is especially assigned to execute the method steps.

The software module can enable a robust and reliable execution of the method and can allow for a fast modification of method steps and/or an adaptation of the image registration algorithm.

In another aspect, the invention provides a method for determining or confirming the presence or absence of ischemia in a patient, said method comprising obtaining medical images of at least a portion of the heart of the subject using an MR, CT or SPECT scanner, using the system as described above, determining a first index number as defined above, and using the results to diagnose the presence or absence of ischemia.

In a particular embodiment, medical images suitable for providing a second index number are also obtained during the method, and the results are used to distinguish between CAD or MVD in an ischemic patient, or to delineate scar tissue in the heart.

In another aspect, the invention provides a storage medium or distribution platform storing a software application comprising the system of the invention as defined herein. For example, the software application may comprise at least the delineation unit and intensity sampler and analyzing unit of the system.

Alternatively, the invention may provide a storage medium or distribution platform storing a software application arranged to carry out the steps carried out by the delineation unit and intensity sampler and analyzing unit of the system as defined herein.

In a further aspect, the invention provides a storage medium or distribution platform storing a software application arranged to determine a first index number as defined herein.

The software application may be further arranged to determine a second index number as defined herein.

Throughout the description and claims of this specification, the words "comprise" and "contain" and variations of the words, for example "comprising" and "comprises", mean "including but not limited to", and do not exclude other components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible.

DETAILED DESCRIPTION OF THE INVENTION

Brief Description of the Figures

The invention will now be particularly described by way of example with reference to the accompanying diagrammatic drawings in which.

EXAMPLE 1

Detection of Ischemia Using System of the Invention

Figure 1A:
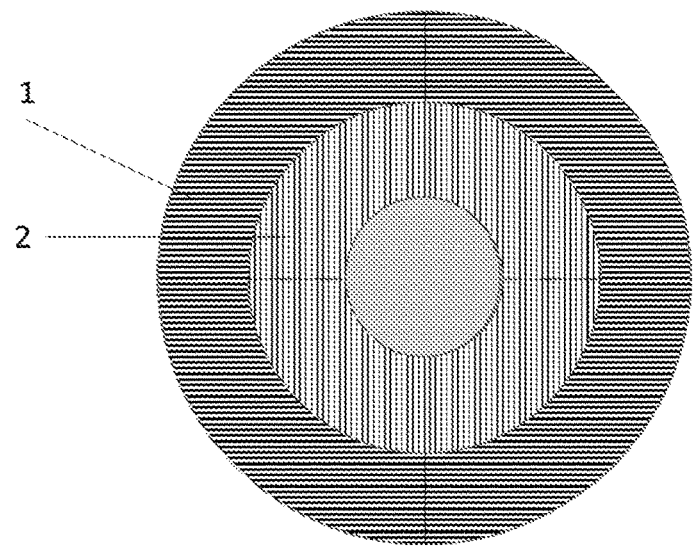
FIG. 1 shows schematically (1A) an epicardium of a heart; (1B) is a schematic of the peak pattern are obtained from first pass analysis in this direction in the epicardial layer, the endocardial layer and the signal vs time at the reference point in the left ventricle in a normal heart; and (1C) is a schematic of the peak pattern are obtained from first pass analysis in this direction in the epicardial layer, the endocardial layer and the signal vs time at the reference point in the left ventricle in an ischemic heart.
Figure 1B:
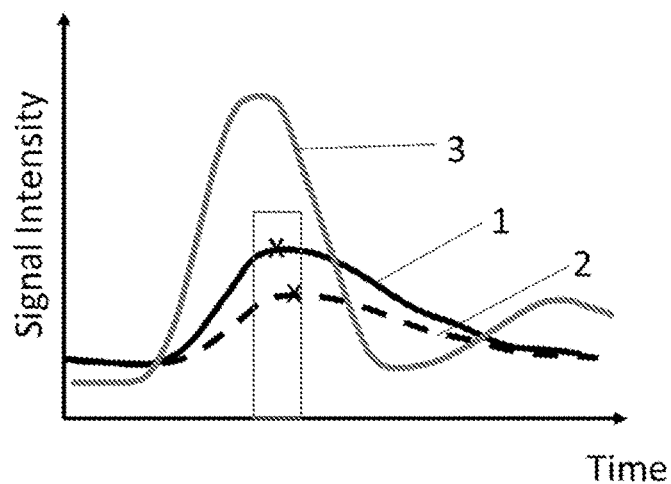
Figure 1C:
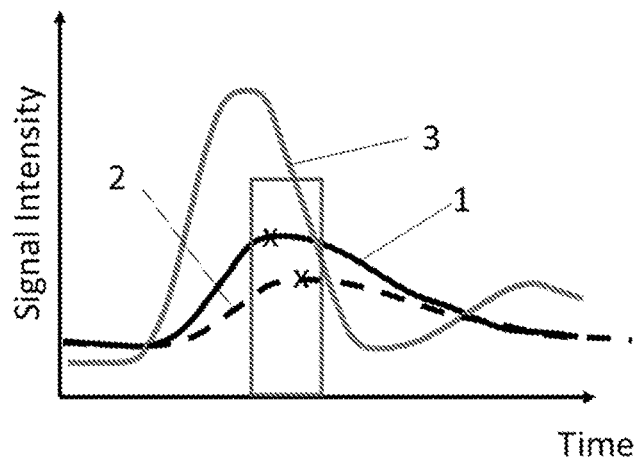

FIG. 1A illustrates schematically an epicardium of the heart, which has been divided into an epicardial layer (1) and an endocardial layer (2) around a central blood vessel. First-pass CT, MR or SPECT images are taken in this direction and signals from the individual layers (1, 2) are determined using the system of the invention. This generates a number of peaks as illustrated in FIGS. 1B and 1C. In these graphs, the signal intensity vs time at the reference point in the left ventricle is shown as the light grey peak (3). The signal intensity versus time peak in the epicardial layer (1) is shown as a solid black line and the signal intensity versus time peak in the endocardial layer (2) is shown as a dashed line. Although peak signal intensity may be expected to vary over time in each of these layers as compared to the reference point, the time to peak intensity TTPI (shown by an 'X' in FIGS. 1B and 1C), may be expected to be similar or vary over only a small range in a normal heart, as illustrated in FIG. 1B.

In a case of ischemia, there will be an inhibition of the flow of blood through the myocardium, giving rise to a more significant difference or spread between the TTPIs between the various layers and the reference point, as illustrated in FIG. 1C. Thus, the TTPI index in this case will be positive, indicative of ischemia in a patient.

EXAMPLE 2

Figure 2A:
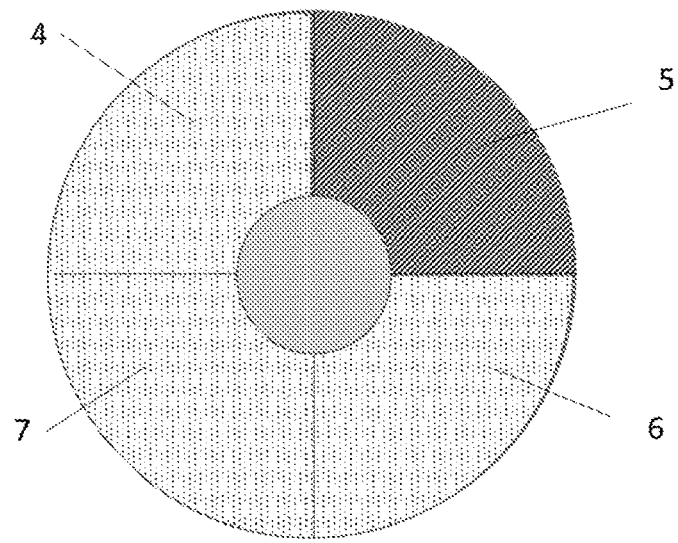
FIG. 2 shows schematically (2A) radial heart segments.
FIGS. 2B and 2C show a schematic of peak patterns that may be obtained from first pass analysis in this direction in the radial direction.
Figure 2B:
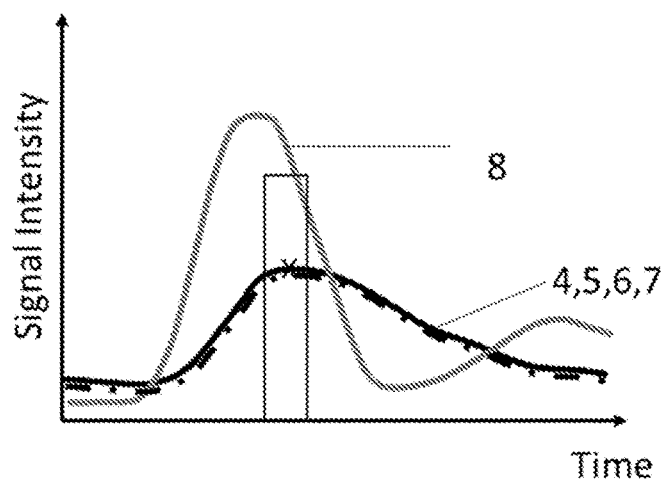

Determination of the Presence of Scar Tissue and Distinction Between CAD and MVD In accordance with a further aspect of the invention, the system is arranged to obtain a further index, based upon measurements taken from a plurality of radial myocardial segments (4,5,6 and 7) in a similar plane to those of the layers used in Example 1 as illustrated in FIG. 2A. In this case, the TTPI index, defined as the difference between the time to peak intensity at the reference point as shown by grey line (8) as compared to the time to peak intensity in all individual radial segments is relatively low in FIG. 2B, with the TTPIs for each of the individual radial segments 4,5,6 and 7, being broadly similar. Where this result follows a positive identification of ischemia as a result of the analysis of Example 1, this provides an indicator that the individual may be suffering from MVD. Alternatively, where the results from Example 1 are negative, this result would confirm that the heart is normal.

Figure 2C:
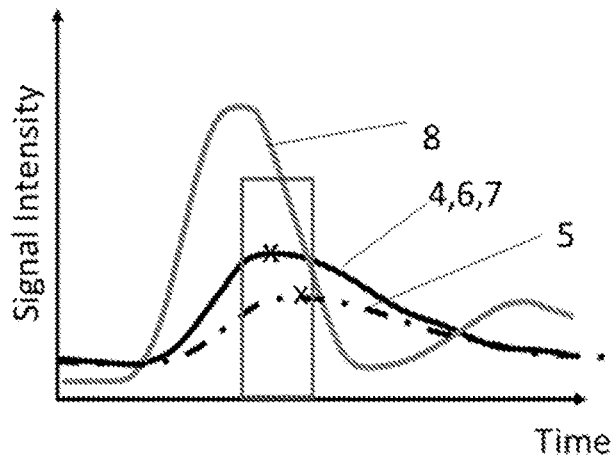

A different result showing a relatively high TTPI is shown in FIG. 2C, with the TTPI of segment 5 being longer than that for segments 4, 6 and 7. Where this result follows a positive diagnosis of ischemia from Example 1, this would suggest that the patient has CAD, which is impeding blood flow in the vessels around segment 5.

However, where this result follows a negative result in Example 1, this suggests that there is scar tissue present in the relevant segment 5, which is causing an abnormal flow rate.

The presence of scar tissue may also be implied in cases where there is only a very slight increase of measured dyssynchrony values in both the radial and transmural directions as compared to the normal heart. Confirmation of the presence of scar tissue may be made by re-sampling of the data in the sample myocardial segments and layers after a period of time, for example after 5 minutes, if necessary in conjunction with late gadolinium (hyper)-enhancement images. In scar tissue, gadolinium would not have cleared the region after that period and so a positive signal would still be present. Once the presence of scar tissue has been identified, these regions may be excluded from future analysis to avoid false negative results in the case of ischemia, and/or false positives for CAD.

If these measurements from Examples 1 and 2 are gathered in a plurality of planes across the myocardium, scar tissue may be effectively mapped in three dimensions.

Once identified, the system may be programmed to exclude results from areas of scar tissue in future analysis.

The invention claimed is:

1. A system for determining the presence or absence of myocardial ischemia in a subject of interest, by analyzing a plurality of medical images of at least one region of the heart of the subject of interest during a first-pass dose of a contrast agent or tracer, the plurality of medical images being in a consecutive manner by a medical imaging modality, the system comprising
    (i) a delineation unit, configured to delineate contours of a selected region of the heart of the subject of interest in the plurality of medical images and to divide the selected region into a plurality of myocardial layers; and
    (ii) an intensity sampler and analyzing unit configured to sample signal intensities of myocardial image positions from the plurality of medical images, and, for each of the myocardial layers, analyse a sampled signal intensity in the selected region over time and compare the results with those obtained at a reference point in the heart to determine a first index number indicative of a spatio-temporal perfusion inhomogeneity or perfusion dephasing among at least a subset of the myocardial layers in the said region as compared to a first comparative index number obtained in normal heart;
and where said first index number is greater than the first comparative index number, diagnosing the presence of ischemia,
    wherein:
        the delineation unit is further arranged to segment at least a selected part of the heart of the subject of interest in the plurality of medical images into a plurality of radial myocardial segments;
        the intensity sampler and analyzing unit is further configured to sample and analyse the medical images obtained over time and, for each of the plurality of radial myocardial segments, analyse a sampled signal intensity over time and compare the results with those obtained at a reference point in the heart to determine a second index number indicative of spatio-temporal perfusion inhomogeneity or perfusion dephasing among at least a subset of radial myocardial segments of the plurality of myocardial segments; compare the second index number to a second index comparative index number obtained in a normal or model heart; and where said second index number is greater, record a positive result; and
    when the presence of ischemia is diagnosed using the first index number, then the second index number is used to distinguish MVD from CAD in the subject of interest.

2. The system of claim 1 wherein the medical imaging modality is selected from a magnetic resonance (MR), computer tomography (CT), positron emission tomography (PET), or single photon emission computed tomography (SPECT) scanner.

3. The system of claim 1 wherein the plurality of myocardial layers is from two to fifty layers.

4. The system of claim 1 which is arranged to analyse images from layers within a plurality of planes in various regions of the heart simultaneously.

5. The system according to claim 1 wherein the second comparative index number is obtained using a model or 'phantom' heart.

6. The system according to claim 1 which is configured to exclude areas of scar tissue from the analysis.

7. The system according to claim 1 which is further configured to correlate the first index number and second index number, and where the first index number is negative or only slightly positive, and the second index number is positive to relate this to the existence of scar tissue in that area.

8. The system according to claim 7 which is configured to obtain a further set of medical images after a period of time and using those images to confirm the presence of scar tissue.

9. The system according to claim 8 wherein the period of time is from 3 to 5 minutes.

10. The system according to claim 8 which is configured to map scar tissue in three-dimensions across the heart.

11. The system of claim 1 which further includes means for conducting quantification of myocardial blood flow in each of the plurality of layers or segments.

12. The system of claim 1 wherein the acquiring of the plurality of medical images of at least a portion of the heart of the subject of interest is at least partially synchronized to a cyclic movement of the heart of the subject of interest.

13. A method for determining or confirming the presence or absence of ischemia in a patient using the system of claim 1, said method comprising obtaining said plurality of medical images of at least a portion of the heart of the subject using imaging modality such as an MR, CT, PET, or SPECT scanner, determining the first index number, using the results to diagnose the presence or absence of ischemia, determining the second index number, and using the results to distinguish between CAD or MVD in an ischemic patient, or to delineate scar tissue in the heart.

14. A non-transitory storage medium storing a software application comprising the system of claim 1.

15. A non-transitory storage medium storing a software application comprising the system of claim 1 arranged to determine the first index number and a second index number.

* * * * *